US006291437B1

(12) United States Patent
Gonczol et al.

(10) Patent No.: US 6,291,437 B1
(45) Date of Patent: Sep. 18, 2001

(54) METHODS AND COMPOSITIONS FOR RETARDING THE DEVELOPMENT OF ATHEROSCLEROTIC LESIONS

(75) Inventors: Eva Gonczol; Klara Berencsi, both of Rosemont, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 08/911,299

(22) Filed: Aug. 14, 1997

Related U.S. Application Data

(60) Provisional application No. 60/023,404, filed on Aug. 14, 1996.

(51) Int. Cl.[7] .......................... A61K 31/70; A61K 39/12; A61K 39/245; C12N 15/00
(52) U.S. Cl. .......................... 514/44; 514/44; 434/199.1; 434/204.1; 434/230.1; 434/233.1; 435/320.1; 435/325
(58) Field of Search .................................. 435/320.1, 236, 435/328, 69.1, 3; 514/44; 424/230.1, 204.1, 199.1, 186.1, 93.1, 233.1

(56) References Cited

U.S. PATENT DOCUMENTS

| 5,424,187 | 6/1995 | Shor ........................................ 435/6 |
| 5,534,258 | 7/1996 | Golubev ............................. 424/231.1 |
| 5,552,143 | * 9/1996 | Plotkin et al. ..................... 424/199.1 |
| 5,591,439 | * 1/1997 | Plotkin et al. ..................... 424/199.1 |

FOREIGN PATENT DOCUMENTS

| WO97/40165 | 10/1997 | (WO) . |
| WO98/33510 | 8/1998 | (WO) . |

OTHER PUBLICATIONS

Melnick et al, BioEssays 17(10):899–903 1995.*
Kuo et al, Proc. Natl. Acad.Sci. USA 92:6911–6914 1995.*
Commentry, Science, 265:320, 1994.*
Melnick et al, J Med. Virol. 42:170–174, 1994.*
Speir et al, Science 265:391–393, 1994.*
Gonczol et al, Vaccine 13(12):1080–1085, 1995.*
Gonczol et al Vaccine 13(12):1080–1085, 1995.*
Endresz et al, Vaccine 17:50–58, 1999.*
Commentary, Science, 265:320, 1994.*
Melnick et al, BioEssays 17(10):899–903, 1995.*
J. Melnick et al, "Possible Role of Cytomegalovirus in Atherogenesis", *JAMA*, 263(16):2204–2207 (Apr. 25, 1990) [Melnick I].
C.–C. Kuo et al, "Demonstration of Chlamydia pneumoniae in Atherosclerotic Lesions of Coronary Arteries", *J. Infect. Dis.*, 167:841–849 (Apr., 1993) [Kuo I].
P. Sorlie et al, "Cytomegalovirus/Herpesvirus and Carotid Atherosclerosis: The ARIC Study", *J. Med. Virol.*, 42:33–37 (1994).

J. Melnick et al, "Cytomegalovirus DNA in Arterial Walls of Patients with Atherosclerosis", *J. Med. Virol.*, 42:170–174 (1994) [Melnick II].
C.–C. Kuo et al, "Chlamydia pneumoniae (TWAR) in Coronary Arteries of Young Adults (15–34) years old)", *Proc. Natl. Acad. Sci. USA*, 92:6911–6914 (Jul., 1995) [Kuo II].
F. Li et al, "Initial Endothelial Injury and Cytomegalovirus Infection Accelerate the Development of Allograft Arteriosclerosis", *Transplantation Proceedings*, 27(6):3552–3554 (Dec., 1995).
J. McEwan, "Potential for Antiviral Therapy in the Treatment of Restenosis After Angioplasty", *Br. Heart J.*, 73:489 (1995).
J. Grayston et al, "Chlamydia pneumoniae (TWAR) in Atherosclerosis of the Carotid Artery", *Circulation*, 92:3397–3400 (Dec. 15, 1995).
C. Mlot, "Chlamydia Linked to Atherosclerosis", *Science*, 272:1422 (Jun. 7, 1996).
J. Muhlestein et al, "Increased Incidence of Chlamydia Species within the Coronary Arteries of Patients with Symptomatic Atherosclerotic Versus Other Forms of Cardiovascular Disease", *J. Am. Coll. Cardiol.*, 27:1555–1561 (Jun., 1996).
G. Ong et al, "Detection and Widespread Distribution of Chlamydia pneumoniae in the Vascular System and its Possible Implications", *J. Clin. Path.*, 49:102–106 (1996).
M. Hendrix et al, "High Prevalence of Latently Present Cytomegalovirus in Arterial Walls of Patients Suffering from Grade III Atherosclerosis", *Am. J. Path.*, 136(1):23–28 (Jan., 1990).
J. Melnick et al, "Cytomegalovirus and Atherosclerosis", *BioEssays*, 17(10):899–903 (Oct., 1995) [Melnick III].
E. Speir et al, "Potential Role of Human Cytomegalovirus and p53 Interaction in Coronary Restenosis", *Science*, 265:391–394 (Jul. 15, 1994).
J. Marx, "CMV–p53 Interaction May Help Explain Clogged Arteries", *Science*, 265:320 (Jul. 15, 1994).

(List continued on next page.)

Primary Examiner—Deborah J. R. Clark
Assistant Examiner—Sumesh Kaushal
(74) Attorney, Agent, or Firm—Howson and Howson

(57) ABSTRACT

A method for preventing or retarding the development atherosclerotic lesions or restenosis involves administering to a subject, preferably a human, an effective amount of an anti-viral composition directed against CMV, and optionally an anti-microbial composition directed against *C. pneumoniae*. These compositions may be conventional chemical anti-microbial pharmaceutics. Alternatively, the compositions may contain a cytomegalovirus (CMV) protein or fragment thereof (or nucleic acid containing compositions expressing such protein or fragment). Such compositions may contain an immunogenic *C. pneumoniae* protein or fragment thereof (or nucleic acid containing compositions expressing such protein or fragment). The protein/nucleic acid compositions are administered in an amount capable of inducing cell mediated immunity and/or antibody response in the subject.

19 Claims, 2 Drawing Sheets

OTHER PUBLICATIONS

G. Steinhoff et al, "Induction of Endothelial Adhesion Molecules by ratCytomegalovirus (CMV) in Allogeneic Lung Transplantation in the Rat", The 5$^{th}$ International CMV Conference, Stockholm (1995) (Abstract No. 025).

W. Waldman et al, "Cytokine–Mediated Induction of Endothelial Adhesion Molecule and HLA Expression by CMV–Activated T Cells", The 5$^{th}$ International CMV Conference, Stockholm (1995) (Abstract No. 026) [Waldman I].

W. Waldman et al, "Bidirectional Transmission of Infectious Cytomegalovirus Between Monocytes and Vascular Endothelial Cells: An in Vitro Model", *J. Infect. Dis.*, 171:263–272 (Feb., 1995) [Waldman II].

A. Grefte et al, "Circulating Cytomegalovirus (CMV)–infected Endothelial Cells in Patients with an Active CMV Infection", *J. Infect. Dis.*, 167:270–277 (Feb., 1993).

J. Grundy et al, "Up–Regulation of LFA–3 and ICAM–1 on the Surface of Fibroblasts Infected with Cytomegalovirus", *Immunology*, 78:405–412 (1993).

E. Pryzdial et al, "Prothrombinase Assembly on an Enveloped Virus: Evidence that the Cytomegalovirus Surface Contains Procoagulant Phospholipid", *Blood*, 84(11):3749–3757 (Dec. 1, 1994).

J. Shih et al, "Possible Role of Viruses in Atherosclerosis", *Nutrition and Biotechnology in Heart Disease and Cancer*, pp. 89–98, ed. J. Longenecker et al, Plenum Press, New York (1995).

B. Plachter et al, "Cell types Involved in Replication and Distribution of Human Cytomegalovirus", *Advances in Virus Research*, 46:195–261 (1996).

C–C. Kuo et al, "Chlamydia Pneumoniae (TWAR)", *Clinical Microbiology Reviews*, 8(4):451–461 (Oct., 1995).

R. Morrison et al, "Chlamydial Disease Pathogenesis, the 57–kD Chlamydial Hypersensitivity Antigen is a Stress Response Protein", *J. Exp. Med.*, 170:1271–1283 (Oct., 1989).

P. Hindmarsh et al, "Final Height of Short Normal Children Treated with Growth Hormone", *Lancet*, 348:13–16 (Jul. 6, 1996).

Y. Zhou et al, "Association Between Prior Cytomegalovirus Infection and the Risk of Restenosis After Coronary Atherectomy", *New Engl. J. Med.*, 335(9):624–630 (Aug. 29, 1996).

J. Grayston, "Infections Caused by Chlamydia Pneumoniae Strain TWAR", *Clin. Infect. Dis.*, 15:757–763 (Nov., 1992).

J. Ramirez et al, "Isolation of Chlamydia Pneumoniae from the Coronary Artery of a Patient with Coronary Atherosclerosis", *Annals of Internal Medicine*, 125(12):979–982 (Dec. 15, 1996).

S.K. Kurz, et al., "Focal Transcriptional Activity of Murine Cytomegalovirus during Latency in the Lungs", *J. Virol.*, 73(1): 482–494 (Jan. 1999) American Society for Microbiology.

A. J. Koffron et al., "Cellular Localization of Latent Murine Cytomegalovirus", *J. Virol.*, 72(1): 95–103 (Jan. 1998) American Society for Microbiology.

N. Saederup et al., "Cytomegalovirus–Encoded B Chemokine Promotes Monocyte–Associated Viremia in the Host", *Proc. Natl. Acad. Sci., USA*, 96:10881–10886 (Sep. 1999).

Mercer et al., "Pathogenesis of Murine Cytomegalovirus Infection: Identification of Infected Cells in the Spleen During Acute and Latent Infections", *J. Virol.*, 62(3):987–997 (Mar. 1988) American Society for Microbiology.

G. M. Keil et al., "Sequence and Structural Organization of Murine Cytomegalovirus Immediate–Early Gene 1", *J. Virol.*, 61(6):1901–1908 (Jun. 1987) American Society for Microbiology.

R. M. Stenberg et al., "Structural Analysis of the Major Immediate Early Gene of Human Cytomegalovirus", *J. Virol.*, 49(1): 190–199 (Jan. 1984) American Society for Microbiology.

Vercellotti, G.M., "Potential Role of Viruses in Thrombosis and Atherosclerosis." *Science*, vol. 5, No. 4, pp1050–1738, (Jul. 1995).

* cited by examiner

METHODS AND COMPOSITIONS FOR RETARDING THE DEVELOPMENT OF ATHEROSCLEROTIC LESIONS

CROSS-REFERENCE TO OTHER APPLICATIONS

This application is a continuation-in-part of pending provisional United States patent application No. 60/023,404 filed Aug. 14, 1996.

FIELD OF THE INVENTION

The present invention relates generally to pharmaceutical compositions and methods of use thereof in treating or preventing atherosclerosis.

BACKGROUND OF THE INVENTION

Atherosclerosis (AT) results from an excessive inflammatory and fibroproliferative response to vascular insult and has been noted to be a principal cause of heart attack and stroke, accounting for up to half of all mortalities in the industrialized world including about 13 million Americans. Atherogenesis is theorized to follow a response to injury, but the agent(s) of injury have yet to be identified fully.

Viral and/or bacterial infection(s) have been found to be associated in some way with the complex process of the development of AT. Particles, antigens and DNA sequences of human cytomegalovirus (HCMV), a member of the herpesvirus group, have been described in AT plaques of biopsy or autopsy material [M. G. Hendrix et al, *Am. J. Pathol.*, 136:23–28 (1990); J. L. Melnick et al., *BioEssays*, 17(10): 899 (October 1995)]. However, Melnick, cited above, states that the "observations do not demonstrate a viral role in the pathogenesis of atherosclerosis". The possible involvement of reactivated HCMV in restenosis of coronary arteries, an accelerated form of AT, following angioplastic surgery has been suggested [S. E. Epstein et al, *Lancet*, 348:13–17 (1996); E. Speir et al, *Science*, 265:391–394 (1994); Y. F. Zhou et al, *N. Engl. J. Med.*, 335: 624–630 (1996)]. Seroepidemiologic data show that HCMV infection usually occurs in childhood, paralleling the pattern of the appearance of early AT lesions; by young adulthood, 50–100% of individuals are HCMV-seropositive. In some individuals, the virus is apparently reactivated in artery walls, where it may initiate abnormal cell growth that can lead to blocked blood flow and, ultimately, heart attack.

The bacterium *Chlamydia pneumoniae* is an intracellular bacterium, which has been established as an important pathogen in acute and chronic respiratory infections [J. T. Grayson, *Clin. Infect. Dis.*, 15:757–763 (1992)] has also been associated with AT [J. A. Ramirez, *Ann. Intern. Med.*, 125:979–982 (1996)]. This bacterium infects about 50% of the population and causes flu-like diseases, but also replicates in the arterial wall. *C. pneumoniae* antigens and DNA have been detected in human AT plaques. Population antibody prevalence studies have shown that more than 50% of adults worldwide have antibody. While antibody is infrequent in children under age 5 years, incidence studies have demonstrated antibody conversion of 6–9% per year in children from the ages 5–14 years. The prevalence of antibody continues to increase throughout adulthood, and is highest in the elderly.

Recently, *C. pneumoniae*, strain TWAR, has been associated with AT based on both seroepidemiology and data demonstrating the presence of the organism in AT plaques. For example, serologic studies from Finland, the United States and other countries have shown that patients with coronary artery diseases were significantly more likely to have serologic evidence of past infection with TWAR than were controls. Morphologic and microbiological evidence of the persistence of TWAR in atheromatous plaques has been obtained by electron microscopic studies, immunochemical staining and PCR testing of coronary, carotid and aortic atheroma [C.-C. Kuo et al, *Clin. Microbiol. Rev.*, 8:451–461 (1995)]. In addition, *C. pneumoniae* activates growth factors involved in inflammatory responses and changes lipoprotein metabolism of infected cells. Immune responses to chlamydial infections are partly protective but also deleterious, and delayed hypersensitivity (DH) is thought to play a pathogenic role in chlamydial disease [R. P. Morrison et al, *J. Exp Med.*, 170:1271–1283 (1989)].

Despite the wealth of reports, no etiological role of HCMV and/or *C. pneumoniae* in the development of AT has been established. Thus, there remains a need in the art for reagents and methods useful in ameliorating the symptoms and development of atherosclerosis in response to these microorganisms.

SUMMARY OF THE INVENTION

In one aspect, the invention provides a method for the treatment or prophylaxis of atherosclerosis in a mammal, preferably a human, comprising administering to a mammal an effective amount of a composition comprising a human cytomegalovirus (HCMV) protein or fragment thereof, the amount capable of inducing cell mediated immunity and anti-CMV antibody response in the mammal. The composition preferably may be administered to infants or immunocompromised patients.

In another aspect the invention provides a method for the treatment or prophylaxis of atherosclerosis in a mammal comprising administering to a mammal an effective amount of a composition comprising a nucleic acid sequence encoding a human cytomegalovirus (HCMV) protein or fragment thereof, said composition capable of inducing cell mediated immunity (CMI) and inducing an anti-CMV antibody response upon expression of said protein in the mammal.

In still another aspect, the invention provides a method for the treatment or prophylaxis of atherosclerosis in a mammal, preferably a human, comprising administering to a mammal an effective amount of a composition comprising a *Chlamydia pneumoniae* protein or fragment thereof, the amount capable of inducing cell mediated immunity and anti-*C. pneumoniae* antibody response in the mammal. The composition preferably may be administered to infants or immunocompromised patients.

In yet another aspect the invention provides a method for the treatment or prophylaxis of atherosclerosis in a mammal comprising administering to a mammal an effective amount of a composition comprising a nucleic acid sequence encoding a *C. pneumoniae* protein or fragment thereof, said composition capable of inducing cell mediated immunity (CMI) and inducing an anti-*C. pneumoniae* antibody response upon expression of said protein in the mammal.

In another aspect, the invention provides a therapeutic or prophylactic composition comprising a *Chlamydia pneumoniae* protein or fragment thereof and an HCMV protein or fragment thereof in a pharmaceutically acceptable carrier.

In still another aspect, the invention provides a therapeutic or prophylactic composition comprising an antimicrobial agent effective against *Chlamydia pneumoniae* infection and an HCMV protein or fragment thereof in a pharmaceutically acceptable carrier.

In yet another aspect, the invention provides a method for treating atherosclerosis or restenosis by administering to a mammal having physical evidence of atherosclerosis or restenosis an effective amount of an anti-microbial agent directed against *Chlamydia pneumoniae* infection.

In a further aspect, the invention provides a method for preventing restenosis after coronary atherectomy or balloon angioplasty comprising treating a patient prior to, or after said atherectomy or angioplasty with an effective amount of said *C. pneumoniae*/HCMV composition described above or with an effective amount of an anti-microbial agent directed against *Chlamydia pneumoniae* infection.

Other aspects and advantages of the present invention are described further in the following detailed description of the preferred embodiments thereof.

DETAILED DESCRIPTION OF THE INVENTION

Figure 1A:
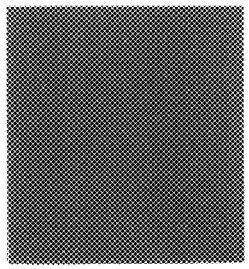
FIG. 1A is a photograph demonstrating viral antigens and chronic inflammatory infiltrate in a section of the aorta of an uninfected mouse. A lack of expression of viral antigens in the endothelial and smooth muscle cells in the aortic wall was detected by immunofluorescence (IF) assay using an anti-murine cytomegalovirus (MCMV) polyclonal mouse serum and FITC labeled second antibody (Chemicon), magnification ×500.

The present invention provides compositions and methods which are useful for both the treatment and prophylaxis of mammalian subjects against the onset or development of atherosclerosis or atherosclerotic lesions characteristic of restenosis or associated with other arterial injury. The invention involves administering anti-microbial compositions directed against HCMV and *C. pneumoniae* to treat and/or prevent the development of atherosclerotic lesions and restenosis.

I. Compositions of the Invention

A. CMV-containing Compositions

The compositions useful according to this invention may contain a CMV protein or fragment. Thus, the composition can be an attenuated, live CMV, preferably HCMV. The composition may also be a heat-inactivated, attenuated HCMV. Vaccines based on live attenuated strains of HCMV have been described. [See, e.g., S. A. Plotkin et al, *Lancet*, 1:528–30 (1984); S. A. Plotkin et al, *J. Infect. Dis.*, 134:470–75 (1976); S. A. Plotkin et al, "Prevention of Cytomegalovirus Disease by Towne Strain Live Attenuated Vaccine", in Birth Defects, Original Article Series, 20(1):271–287 (1984); J. P. Glazer et al, *Ann. Intern. Med.*, 91:676–83 (1979); and U.S. Pat. No. 3,959,466, all incorporated by reference herein.]

Alternatively, the composition may contain only certain HCMV proteins or fragments of these proteins which are characterized by the capacity to induce cell mediated immunity (CMI) to CMV infection upon administration of the protein in combination with an appropriate adjuvant. This composition may induce a low to undetectable anti-CMV antibody response in the subject. Desired HCMV proteins for this use include, without limitation, phosphoproteins 65, 150, 28 and 52, immediate early protein (IE), glycoprotein B (gB), and glycoprotein H (gH). Most desirably, the early HCMV proteins IE, gB and pp65 are useful in such a composition. One example of a useful fragment for this purpose is the immediate-early exon-4 (IE-exon-4) subunit of the HCMV. [See, e.g., International Patent Application No. WO94/17810, published Aug. 18, 1994, incorporated by reference herein].

Where the HCMV composition contains nucleic acid sequence(s) encoding a cytomegalovirus protein or fragment thereof, the nucleic acid sequence may be that of the selected protein itself, that is, a 'naked' DNA composition. So-called 'naked DNA' may be used to express the HCMV protein or peptide fragment in vivo under the control of suitable promoter sequences. [For a discussion of this technology, see, e.g., J. Cohen, *Science*, 259:1691–1692 (Mar. 19, 1993); E. Fynan et al, *Proc. Natl. Acad. Sci.*, 90: 11478–11482 (December 1993); J. A. Wolff et al, *Biotechniques*, 11:474–485 (1991), all incorporated by reference herein, which describe similar uses of 'naked DNA']. For example, HCMV DNA encoding the IE protein under control of the HCMV-IE promoter may be used as an HCMV composition and administered according to the method of this invention. Other suitable homologous or heterologous promoter sequences may readily be selected, and the sequence constructed by methods known in the art.

Alternatively, the nucleic acid sequence composition may contain a vector which carries the CMV protein-encoding DNA under the control of regulatory sequences which are capable of directing the expression of the product of the sequence. Such vectors may be viral in origin. For example, a proposed HCMV vaccine using a recombinant vaccinia virus expressing HCMV glycoprotein B has been described. [See, e.g., Cranage, M. P. et al, *EMBO J.*, 5:3057–3063 (1986).] Additionally, an adenovirus vector carrying an HCMV protein sequence or fragment has been described. [See, e.g., International Patent Application No. WO94/17810, published Aug. 18, 1994 and International Patent Application No. WO94/23744, published Oct. 27, 1994]. Other viral vectors, such as canarypox virus or a retrovirus may also be employed as carriers for the nucleic acid sequences of HCMV proteins or fragments.

Similarly, such vectors may be non-viral in origin, such as known bacterial-based plasmids, e.g., pBR322 or pUC, or mammalian-based plasmids and may be employed to deliver the HCMV sequences to the subject. Many suitable plasmids are known to those of skill in the art and may be designed to contain the selected HCMV protein-encoding sequences.

As stated above for the protein compositions, the desired HCMV protein sequences or DNA sequences encoding them preferably are those HCMV proteins which readily induce CMI. Other HCMV proteins which may be desirable for use in this invention may induce low or undetectable amounts of antibody in the subject. It is presently preferred to use the HCMV protein sequences such as pp65, IE, and fragments thereof, such as IE exon 4.

The compositions of this invention may also employ more than one HCMV protein or fragment, or proteins and fragments from more than one strain of HCMV, or the nucleic acid sequences encoding same.

B. *C. pneumoniae*-containing Compositions

The compositions useful according to this invention are anti-microbial compositions directed against a *C. pneumoniae* infection.

In one embodiment, such compositions may be conventional antibiotics effective against many pneumonias, such as tetracycline, erythromycin and other conventional pharmaceutical antibiotic agents known to the skilled artisan.

In another embodiment an anti-microbial composition useful in this invention may contain an immunogenic *C. pneunoniae* protein or fragment, e.g., the major outer membrane protein. Thus, the composition can be a killed *C. pneumoniae* of any suitable strain. Vaccines based on killed strains of *C. pneumoniae* may be prepared by conventional techniques of heat or irradiation.

Alternatively, the composition may contain only certain *C. pneumoniae* proteins, e.g., the major outer membrane protein, or fragments of these proteins which are characterized by the capacity to induce cell mediated or humoral immunity to *C. pneumoniae* infection upon administration of the protein in combination with an appropriate adjuvant. This composition may induce a low to undetectable anti-*C. pneumoniae* antibody response in the subject. A desired *C. pneumoniae* protein or peptides for this use is desirably a bacterial cell surface protein, which may be randomly fragmented. Random fragments of a *C. pneumoniae* protein may be readily tested for immunogenicity by one of skill in the art, using a variety of assay formats. Vaccines containing *C. pneumoniae* cellular antigens or fragments may be obtained conventionally, e.g., by cell lysis and standard purification or separation techniques.

Where the *C. pneumoniae* composition contains nucleic acid sequence(s) encoding a surface protein or fragment thereof, the nucleic acid sequence may be that of the selected protein itself, that is, a 'naked' DNA composition. So-called 'naked DNA' may be used to express the *C. pneumoniae* protein or peptide fragment in vivo under the control of suitable promoter sequences. [See the references cited above discussing naked DNA].

Alternatively, the nucleic acid sequence composition may contain a vector which carries the *C. pneumoniae* protein-encoding DNA under the control of regulatory sequences which are capable of directing the expression of the product of the sequence. One particularly desirable embodiment is a vector encoding the major outer membrane protein. Suitable vectors may be selected from among known viral and plasmid vectors as described above for the HCMV compositions.

As stated above for the protein compositions, the desired *C. pneumoniae* protein sequences or DNA sequences encoding them preferably are those *C. pneumoniae* proteins which readily induce CMI. Other *C. pneumoniae* proteins which may be desirable for use in this invention may induce low or undetectable amounts of antibody in the subject.

The compositions of this invention may also employ more than one *C. pneumoniae* protein or fragment, or proteins and fragments from more than one strain of *C. pneumoniae*, or the nucleic acid sequences encoding same.

C. Combination Compositions

The present invention also provides for compositions which comprise both an anti-microbial agent directed against a *C. pneumoniae* infection and an anti-viral composition directed against HCMV in a suitable pharmaceutical carrier.

For example, a combination composition of the present invention may contain an HCMV protein containing composition such as described above and a *C. pneumoniae* protein composition as described above. Alternatively, a naked DNA composition may contain the DNA of an HCMV protein or fragment and a *C. pneumoniae* protein or fragment as described above. Similarly a composition may contain a mixture of plasmid or viral vectors individually bearing DNA sequences which encode an HCMV protein or fragment and a *C. pneumoniae* protein or fragment, as described above.

Another alternative combination composition may comprise a polycistronic vector, which carries the DNA sequence which encodes an HCMV protein or fragment and the DNA sequence which encodes a *C. pneumoniae* protein or fragment. These fragments may be under the control of the same regulatory sequence which directs expression of both proteins in vivo. Alternatively, the polycistronic vector may contain separate regulatory sequences for each protein to be expressed.

Another embodiment of the composition of the present invention comprises the use of a conventional pharmaceutical antibiotic active against *C. pneumoniae* combined with an HCMV protein/DNA compositions as described above in a suitable pharmaceutical carrier.

A similar embodiment of the composition of the present invention comprises the use of a conventional pharmaceutical antiviral useful against HCMV infection combined with a *C. pneumoniae* protein/DNA composition as described above in a suitable pharmaceutical carrier.

II. Production of the Compositions

HCMV isolates, *C. pneumoniae* strains, proteins and fragments of these microorganism, and their DNA sequences may be obtained in a variety of conventional ways. For example, strains of HCMV useful in the practice of this invention may be obtained from depositories, such as the American Type Culture Collection, Rockville, Md. (ATCC) or from other institutes or universities. Similarly, strains of *C. pneumoniae*, e.g., the TWAR strain, are available from the ATCC under Accession Nos. VR1310, 1355, 1356, 1360 and 2282, among others. Other strains may also be obtained from institutes or universities.

The preparation of heat-inactivated, or live attenuated viral and bacterial preparations are known to the art as provided by the publications incorporated above. Alternatively, protein sequences may be isolated by conventional techniques from the many available strains. The sequences of the subunits of two HCMV strains have been published [See, e.g., Mach et al, *J. Gen. Virol.*, 67:1461–1467 (1986); Cranage et al, (1986) cited above; and Spaete et al, *Virol.*, 167:207–225 (1987)]. These sequences, and other known HCMV sequences, can be chemically synthesized by conventional methods known to one of skill in the art, [Sambrook et al, "Molecular Cloning", 2nd ed., Cold Spring Harbor, N.Y. (1989)] or the sequences purchased from commercial sources.

Similarly fragments of *C. pneumoniae* surface proteins may be randomly fragmented by conventional means, e.g., restriction enzymes, and sequenced and chemically synthesized by employing the same protocols.

In the practice of another embodiment of this invention the HCMV protein or fragment and/or the *C. pneumoniae* immunogenic protein or fragment may be produced in vitro by recombinant techniques in large quantities sufficient for use in a composition of this invention. Alternatively, a recombinant virus or plasmid vector carrying the HCMV protein or fragment and/or *C. pneumoniae* protein or fragment may be prepared by conventional techniques of genetic engineering. See, for example, the techniques described in the above-cited international patent applications, incorporated by reference herein.

The preparation of a pharmaceutically acceptable composition containing the HCMV and/or *C. pneumoniae* protein(s) or DNA sequence(s), having appropriate pH, isotonicity, stability and other conventional characteristics is within the skill of the art. These pharmaceutical compositions may optionally contain other components, such as adjuvants, e.g., aqueous suspensions of aluminum and magnesium hydroxides, and/or pharmaceutically acceptable carriers, such as saline.

It is anticipated that CMV other than HCMV, and various strains of *C. pneumoniae* may be used to design compositions useful to prevent analogous conditions in various animal species, i.e., domestic animals and other valuable animals.

III. Methods of the Invention

Without wishing to be bound by theory, and as described in more detail herein, the inventors theorize, and their preliminary results suggest, that AT is a multifactorial process, with CMV and/or *C. pneumoniae* infections initiating development of the disease. Reactivation of these pathogens as well as genetic factors related to lipid metabolism contribute to the disease. CMV is involved in two of the major mechanisms that lead to the development of AT. The first is efficient infection of cells in the inner layer of arteries in vivo and induction of and injury at the area of infection corresponding to early AT lesions. The second mechanism is an increase in serum levels of low-density lipoprotein cholesterol, a major lipid contributor to AT plaques. It is anticipated that chronic infection with periodic reactivations, typical of human CMV infections, leads to full-blown AT. Additionally, seroepidemiologic data and direct isolation of *Chlamydia pneumoniae* from human AT plaques also suggest the involvement of this bacterium in the development of AT. Coinfection or consecutive infection of the arterial wall with CMV and *C. pneumoniae* likely increase the cellular damage of the intima that leads to the development of mature AT plaques.

Thus, the invention provides preventive and therapeutic compositions and methods that reduce the incidence of these closely related infections in certain subjects and hence those conditions and diseases characterized by injury to arterial vessels. Suitable subjects for treatment with the compositions and methods of the present invention include mammals, preferably humans, (a) who are anticipating immunosuppression due to organ or bone marrow transplant (for administration before, during or after the transplant); (b) pre-atherosclerotic subjects seeking prophylaxis of atherosclerosis, e.g., human children or infants; (c) subjects with existing atherosclerosis, e.g., human adults; (d) subjects who have restenosis, an accelerated form of AT, which is the narrowing of coronary arteries that occurs in about half of patients after coronary atherectomy and balloon angioplasty; and (e) subjects seeking to prevent or ameliorate the occurrence of restenosis, i.e., patients anticipating coronary atherectomy or balloon angioplasty, or post-surgical patients, among others. It should be understood that any injury to an arterial vessel, either existing or anticipated, can benefit by the use of the present invention.

According to one embodiment of this invention, a subject is administered an effective amount of a composition which contains either (a) a human cytomegalovirus (HCMV) protein or fragment thereof, or (b) a nucleic acid sequence encoding HCMV protein or fragment thereof. In either case, the composition is administered in an amount sufficient to induce CMI and humoral immunity to CMV infection and prevent, or retard, the development of atherosclerotic lesions.

According to another embodiment of this invention, a subject is administered an effective amount of a composition which contains either (a) a *C. pneumoniae* protein or fragment thereof, or (b) a nucleic acid sequence encoding said protein or fragment thereof. In either case, the composition is administered in an amount sufficient to induce CMI and humoral immunity to *C. pneumoniae* infection and prevent, or retard, the development of atherosclerotic lesions.

According to yet another embodiment of this invention, a subject is administered an effective amount of a composition which contains a combination of (a) a *C. pneumoniae* protein or fragment thereof and a human cytomegalovirus (HCMV) protein or fragment thereof, or (b) a nucleic acid sequence encoding said *C. pneumoniae* protein or fragment thereof and a nucleic acid sequence encoding HCMV protein or fragment thereof. In either case, the composition is administered in an amount sufficient to induce CMI and humoral immunity to both *C. pneumoniae* and HCMV infection and prevent, or retard, the development of atherosclerotic lesions due to either infective agent.

Still another embodiment of this invention is a treatment method by which a subject as described above is administered an effective amount of an anti-microbial composition effective in treating *C. pneumoniae* infection. Such a method may further include contemporaneous treatment (i.e., before, during or after administration of the anti-microbial agent) with a composition containing either a cytomegalovirus (HCMV) protein or fragment thereof, or a nucleic acid sequence encoding said HCMV protein or fragment thereof, the HCMV-containing composition administered in an amount sufficient to induce CMI and humoral immunity to HCMV infection. Such a method enables the prevention or retardation of the development of atherosclerotic lesions due to either infective agent.

Still another novel treatment or prophylactic method of this invention involves the use of a composition which contains a combination of an immunogenic *C. pneumoniae* protein or fragment thereof and an antiviral composition directed against human cytomegalovirus. Another embodiment of this method may also employ a nucleic acid sequence encoding the *C. pneumoniae* protein or fragment thereof. In either case, the *C. pneumoniae*-containing composition is administered in an amount sufficient to induce CMI and humoral immunity to *C. pneumoniae*. This method enables the prevention or retardation of the development of atherosclerotic lesions due to either infective agent.

According to the present invention, the selected composition described above is administered preferably as a vaccine to infants. Subsequent periodic boosters may be administered as for other vaccines.

Alternatively, the method involves administering the compositions of the present invention to patients prior to, or immediately after, undergoing organ or bone marrow transplants, blood transfusions, or other immunosuppressive treatments. Organ transplant patients can develop atherosclerosis very quickly in a transplanted organ, either through the organ itself or through blood transfusions. Thus, the method of this invention is useful for treating organ transplant, or otherwise, immunosuppressed patients, following the transplantation.

Still another alternative method of the invention involves administering one of more of the described compositions to a balloon angioplasty or coronary atherectomy patient, either before, during or after the surgical procedure to prevent or reduce the development of restenosis.

It is anticipated that therapeutic treatments of compositions described above to adult subjects having some existing degree of atherosclerosis is also useful to slow the advance of the condition and/or prevent or reduce further injury, i.e., the occurrence of atherosclerotic injury to blood vessels.

Another clinical setting for which the methods of the present invention are useful is for a woman planning pregnancy. To avoid passage of CMV to a fetus, which, when it occurs, causes congenital malformations and heart complications, a woman planning a pregnancy may be treated with a CMV composition according to this invention.

For the compositions containing proteins, the preferred dosage ranges from about 10 to about 80 micrograms of protein. In a combination composition, the dosages of each protein are at the lower end of that range. Preferred dosages, in general, are the lower end of that range. When a recombinant virus vector is administered as the pharmaceutical composition, a dosage of between $10^5$ and $10^7$ plaque forming units of each vector may be used. Preferred dosages are the lower end of that range. When naked DNA is administered as the pharmaceutical composition, a dosage of between 50–200 micrograms may be used. Preferred dosages are the lower end of that range. Dosages of conventional antibiotics are administered by conventional routes and dosages ordinarily prescribed for such pharmaceutical compositions and these may also be determined by the attending physician.

Additional similar, repeated doses of the protein/nucleic acid sequence-containing compositions of this invention may also be administered at a desired interval, i.e., at 1–10 year intervals, where considered desirable by the physician. The dosage regimen involved in the method for treating or preventing atherosclerosis with such compositions can be determined considering various clinical and environmental factors known to affect such administration.

The route of administration may be oral, nasal or subcutaneous, particularly where the virus vector composition is used. However, another route of administration may include intramuscular injection. The route of administration depends upon the particular composition selected for such use, and may readily be selected by the attending physician.

The following examples illustrate various aspects of this invention and do not limit the invention, the scope of which is embodied in the appended claims. BALB/c and C57BL/6 mice were used in these experiments.

EXAMPLE 1

Development of Early Atherosclerotic Lesions in Mice Infected with Murine CMV

A. Infection

Mice were infected with murine CMV (Smith strain; ATCC VR-194) at a dose of $1 \times 10^6$ pfu via the intraperitoneal (i.p.) route on day 1. Fifty-five days post infection, the mice were sacrificed and the heart was obtained and sectioned above the right and left auricles. These tissues were subjected to a conventional immunofluorescence assay using anti-MCMV polyclonal antibody.

Endothelial cells (EC) and smooth muscle cells (SMC) of the mouse aortic wall express viral antigens after MCMV infection. Accumulation of inflammatory and SMCs in the aortic lumen at the site of viral antigen expression has been observed and defined as early atherosclerotic lesions.

B. Additional Experiments

In the next series of experiments, mice were infected i.p. with the parental strain of MCMV at a dose of $1 \times 10^4$ pfu, γ-irradiated at the time of infection (day 0) or non-irradiated, and fed an atherogenic or normal diet. Mice were sacrificed on day 36, hearts were obtained and sectioned for viral antigen expression and pathological changes.

Figure 1B:
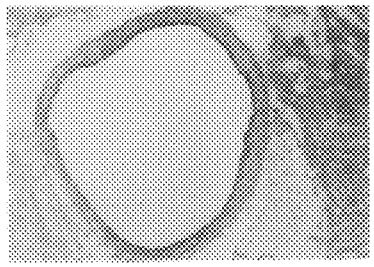
FIG. 1B is a photograph demonstrating viral antigens and chronic inflammatory infiltrate in a section of aorta from the same mouse showing no accumulation of inflammatory cells in the aortic lumen. This is a parallel section stained with hematoxilin-eosin (HE), magnification ×500.
Figure 1C:
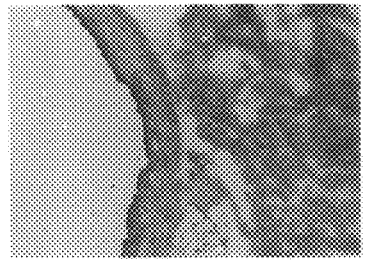
FIG. 1C is a photograph demonstrating viral antigens and chronic inflammatory infiltrate in a parallel section of the aorta of the uninfected mouse as described in FIG. 1B, except that magnification was ×1250.

FIGS. 1A–1C show sections of a naive mouse, with no reactivity with the anti-MCMV antibody in the immunofluorescence (IF) test and with no inflammatory reaction in the aortic wall and lumen. FIGS. 1G–1I show large areas of virus antigen expression with adherent inflammatory cells on the luminal surface of the aorta from a mouse infected, immunosuppressed and fed a normal diet. The inflammatory infiltrate consists of many large lymphocytes and plasma cells with a few monocytes and peripheral mononuclear cells. Similar expression of viral antigens and inflammatory reactions was detected in the aortic wall of a mouse infected, immunosuppressed, and fed an atherogenic diet. Small areas of the aortic wall with expression of MCMV antigens and accumulation of inflammatory cells at a site of viral antigen expression in a mouse infected, not immunosuppressed, and fed cholesterol or normal diet were also observed. Mice not infected but fed a cholesterol diet, or not infected but irradiated, showed neither viral antigen expression nor inflammatory changes in the aorta.

These data show that an acute MCMV infection of mice induces a vascular wall inflammation that may play a role in the immune injury of the vascular structure and thus initiate the development of AT.

C. Immunosuppression

Mice were infected with murine CMV (Smith strain) by the same procedure as described above. The mice were exposed to gamma-irradiation (500 rad) at the time of infection. Thirty-six days post infection, the mice were sacrificed and various tissues were examined as described above.

Figure 1D:
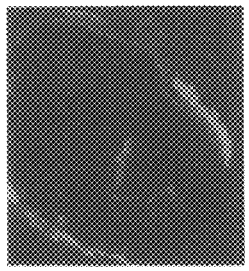
FIG. 1D is a section of aorta from a mouse infected with the Smith strain of MCMV (ATCC Accession No. VR194), γ-irradiated (500 rad) and fed with a high cholesterol diet. This section shows the expression of viral antigens in the endothelial and smooth muscle cells in the aortic wall as detected by IF assay using anti-MCMV polyclonal mouse serum.
Figure 1E:
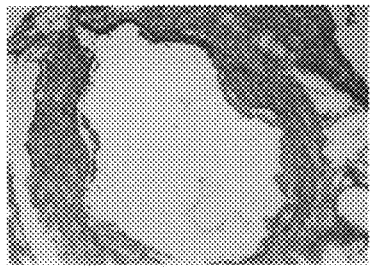
FIG. 1E is a section from the mouse of FIG. 1D, showing accumulation of inflammatory cells in the aortic lumen and in the periaortic area in a parallel section stained with HE, magnification ×500.
Figure 1F:
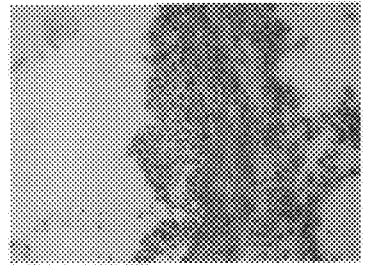
FIG. 1F is a parallel section as described in FIG. 1E, except that magnification was ×1250.
Figure 1G:
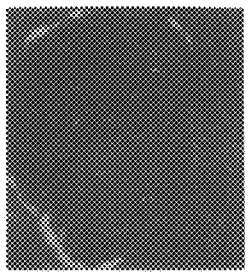
FIG. 1G is a photograph demonstrating viral antigens and chronic inflammatory infiltrate in a section of aorta from a mouse infected with the Smith strain of MCMV, γ-irradiated (500 rad) and fed with a normal mouse diet. This section shows the expression of viral antigens in the endothelial and smooth muscle cells in the aortic wall as detected by IF assay using anti-MCMV polyclonal mouse serum and FITC labeled second antibody (Chemicon), magnification ×500.
Figure 1H:
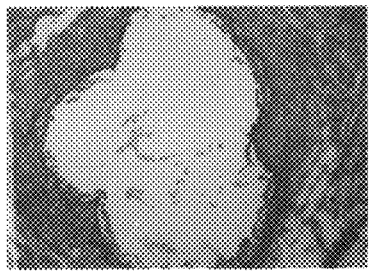
FIG. 1H is a photograph demonstrating viral antigens and chronic inflammatory infiltrate in a section of aorta from the mouse of FIG. 1G, showing accumulation of inflammatory cells in the aortic lumen and in the periaortic area in a parallel section stained with HE, magnification ×500.
Figure 1I:
FIG. 1I is a photograph demonstrating viral antigens and chronic inflammatory infiltrate in a parallel section of the aorta of the mouse described in FIG. 1H, except that magnification was ×1200.
Figure 1J:
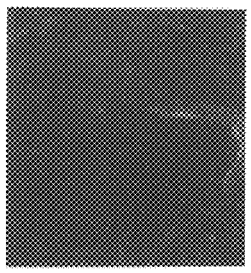
FIG. 1J is a section of aorta from a mouse infected with the Smith strain of MCMV, not γ-irradiated, and fed with a normal mouse diet. This section shows the expression of viral antigens in the endothelial and smooth muscle cells in the aortic wall as detected by IF assay using anti-MCMV polyclonal mouse serum.
Figure 1K:
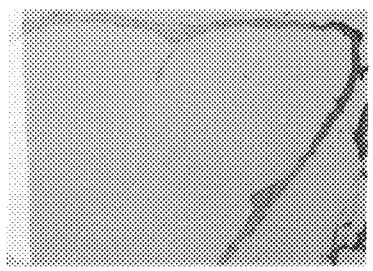
FIG. 1K is a section from the mouse of FIG. 1J, showing accumulation of inflammatory cells in the aortic lumen and in the periaortic area in a parallel section stained with HE, magnification 1:630. A small area of accumulation of inflammatory cells is seen in the right upper corner of the aorta.
Figure 1L:
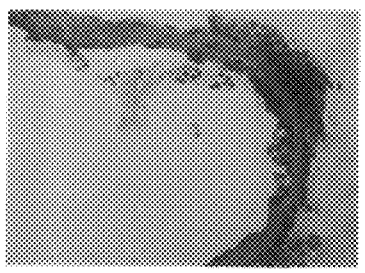
FIG. 1L is a parallel section as described in FIG. 1K, except that magnification was 1:1575.

Immunosuppression by gamma-irradiation at the time of virus infection increased the virus titer in salivary glands from $1-5 \times 10^3$ to $0.5-2.5 \times 10^4$ pfu/salivary glands and extended the size of the expression of viral antigens in the aortic wall from about 2/10 of aortic wall (FIG. 1J) to 5/10 (FIG. 1G) or 7/10 (FIG. 1D). Accumulation of inflammatory cells in the lumen and in the periaortic area was seen at the region where viral antigen expression was detected in mice not irradiated (FIGS. 1J–1L). More irradiated inflammatory cells were seen throughout the aortic lumen.

D. High Cholesterol Diet

Another group of mice was fed a high cholesterol Western diet designed to elevate plasma cholesterol levels for 1 week, then infected with MCMV as described in the assays above. Fifty-five days post infection, the mice were sacrificed and vascular tissues were examined as described above.

The high cholesterol diet had no significant synergistic effect on the development of early atherosclerotic lesions at the site of viral antigens.

E. Serum Cholesterol—in vivo Assay

Three groups of mice were treated as follows: One group was fed with a high cholesterol diet and infected with MCMV; a second group was fed with a normal diet and infected with MCMV, and a third group was not infected and used as a control. After fifty-five days post infection (or on the analogous day for the controls), serum from each group of mice was collected and assayed for total cholesterol and triglycerides using a commercially available (Sigma) kit.

Analysis of the sera of each group demonstrated that the serum level of low density cholesterol (LDC), a major lipid component of lipid-leded macrophages and other cells in the atherosclerotic plaques, is significantly increased in mice infected with MCMV, either fed with atherosclerotic diet (as in Part C above) or not, as compared with uninfected mice.

F. Lipid Metabolism—in vitro Assay

A human arterial smooth muscle cell line (cells No. 101 obtained from Dr. Elliot Levine, The Wistar Institute, Philadelphia, Pa.) was infected in vitro with human CMV at a multiplicity of infection (MOI) of 1–2. After five days, the cells were extracted with chloroform-methanol 2:1 and lipid extract analyzed for total and free cholesterol using standard methodology.

In the infected cells, the esterified cholesterol component of the total cholesterol was 29.7%, as compared with the undetectable level of esterified cholesterol in uninfected cells. These results, and those of part D above, indicate that both HCMV and MCMV disturb lipid metabolism in infected cells and change it in the direction of the accumulation of lipid elements, contributing to the development of atherosclerotic plaques.

EXAMPLE 2

Treating Mice with CMV Compositions

Tissue culture-adapted (attenuated) MCMV (ATCC No. VR-104) was grown in tissue culture fibroblasts prepared from BALB/c embryos by conventional techniques. Alternatively, the tissue culture-adapted MCMV was inactivated by treatment with heat at 56° C. for 30 minutes.

BALB/c mice (10 in each group) were immunized i.p. with either the live attenuated MCMV at a dose of $1 \times 10^6$ pfu in a volume of 0.1 ml or the inactivated virus (0.1 ml) on day 0. Mice received a booster inoculation three weeks after the first inoculation. A group of mice was not immunized for use as controls.

Five weeks after the second inoculation, all mice were challenged with $3 \times 10^6$ pfu live virulent MCMV, which was grown in vivo in murine salivary glands. On day 10 after the challenge, the mice were sacrificed and their vascular tissue examined by immunofluorescence (IF) assay using an anti-murine cytomegalovirus (MCMV) polyclonal mouse serum.

The control mice were found to have viral antigen expression in the aortic wall and in smooth muscle cells of the heart, and early atherosclerotic lesions. However, mice immunized with either live attenuated, or heat inactivated, attenuated MCMV were found to have no such lesions. Thus, the live or inactivated attenuated MCMV compositions protected the mice from the development of viral antigen expression and early atherosclerotic lesions following live virulent viral infection, indicating that the development of atherosclerosis is preventable.

EXAMPLE 3

Mice Infected with HCMV

This example demonstrates the effect on the development of early atherosclerotic lesions in the mouse aortic intima of infection of mice with HCMV.

HCMV does not replicate in mouse cells, but expresses immediate early (IE) antigens. The expression of CMV IE antigens may be sufficient to cause such lesions. This theory is tested by examining attachment of inflammatory cells and SMCs to the intima, expression of IE antigens and cellular adhesion molecules in the ECs and SMCs.

BALB/c mice are injected i.v. with live purified HCMV at a dose of $10^4-10^6$ pfu. Two to twenty days after infection, mice are sacrificed, heart sections obtained as described above, and expression of IE antigens is tested by IF assay using a monoclonal antibody specific to IE antigens (e.g., E13, Chemicon). The presence of early atherosclerotic lesions is analyzed on consecutive sections stained with hematoxilin-eosin. The presence of significant lesions indicates that IE expression alone can cause early atherosclerotic damage.

EXAMPLE 4

Latency Murine CMV Model of HCMV Infection

This experiment describes a latency CMV murine model which mimics the course of HCMV infection in humans:

Mice are inoculated with MCMV, thereby establishing an acute infection, and tissue is tested for atherosclerotic lesions and expression of CMV viral antigens as described above. After the virus becomes latent, i.e., 3–4 weeks, the same tests are performed and viral antigens are not expressed.

Mice are then immunosuppressed, preferably by gamma irradiation to reactivate the CMV infection. The same tests as described above are performed and viral antigens are again expressed. After the virus again becomes latent, the tissues are examined and viral antigens are no longer expressed.

A periodic increase in the severity of atherosclerotic lesions accompanies the periodicity of virus reactivation.

A second set of mice are similarly treated as above, but immunized with the selected CMV composition either before acute infection or in the latency stage. Comparison of atherosclerotic lesions in control mice vs. immunized mice at the various stages of the model demonstrates the efficacy of immunizing the mice with a CMV composition of this invention to prevent the development or further progression of such lesions.

EXAMPLE 5

Rabbit Model of HCMV

The rabbit is a well-established model for experimental atherosclerosis. Rabbits are infected with HCMV or MCMV and the aortic tissue tested as above described for expression of IE antigens, as well as for the development of fatty streaks, i.e., the early lesions of atherosclerosis (AT). Since the rabbit aorta is considerably larger than the mouse aorta, the fatty streaks are visible macroscopically.

Once AT lesions develop in the rabbit aorta after CMV infection, the CMV compositions described herein are tested for the ability to protect the animal against further progression of AT lesions.

EXAMPLE 6

Development of Early Atherosclerotic Plaques and Antigens

A. BALB/c and C57BL/6 mice were infected i.p. with either $1 \times 10^4$ pfu a recombinant MCMV expressing the bacterial β-galactosidase (lacZ) gene (MCMV-lacZ) [C. A. Stoddart et al, *J. Virol.*, 68:6243–6253 (1994)(gift of Dr. E. Mocarski, Stanford University, Stanford, Calif.), or with the same dosage of the parental MCMV (Smith strain, ATCC VR-194). BALB/c mice were infected i.p. with $1 \times 10^4$ pfu of MCMV-lacZ virus, and immunosuppressed by γ-irradiation (450 rad) at the time of infection to slow down virus clearance, and fed either an atherogenic diet (8% coconut oil, 2% soybean oil, 0.5% cholesterol) or a normal mouse diet. Uninfected mice were treated similarly. Mice were sacrificed 25 days after virus infection, and hearts were obtained and sectioned as described in B. Paigen et al, *Atheroscl.*, 68:1614–1620 (1987). Sections were treated with X-gal to detect lacZ-expressing cells indicating virus replication, or stained with H&E for pathological changes or with oil red 0 for lipid accumulation in the tissues.

An inflammatory response developed in the aortic wall of the mice, similar to early AT lesions in humans, and lipid metabolism shifted to high levels of serum LDL-C, a major contributor to AT plaques. MCMV-lacZ replicated and induced inflammatory reactions at the site of replication in the aortic wall (FIG. 2A).

Figure 2A:
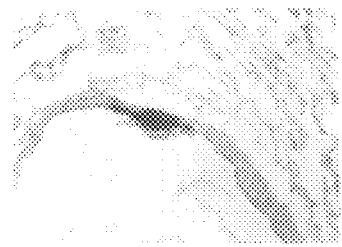
FIG. 2A illustrates LacZ expression and an early AT plaque in aorta of a MCMV-lacZ-infected mouse at magnification ×500.
Figure 2B:
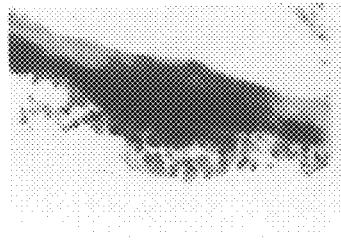
FIG. 2B is the photograph of FIG. 2A at magnification ×1250.
Figure 2C:
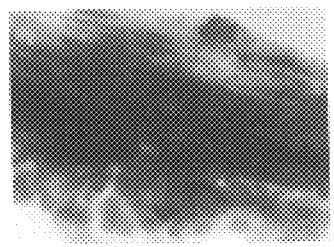
FIG. 2C is the photograph of FIG. 2A at magnification ×2500.

In mice infected with MCMV-lacZ, irradiated and fed an atherogenic diet, lacZ was expressed in the endothelial and smooth muscle cells of the aorta (FIGS. 2A–2C). An early AT plaque at the site of virus replication with inflammatory cells in the lesion and below it through the thickness of the aorta was also seen (FIG. 2A–2C). Oil red O staining revealed lipid in this same area (not shown). Mice infected with the virus, irradiated and fed a normal mouse diet also showed lacZ-expression in the salivary gland and arterial adventitia associated with adventitial vacuoles, in a few muscle cells in the heart (not shown). Mice infected with the virus, irradiated and fed a normal mouse diet also showed lacZ-expression in the salivary gland and arterial adventitia associated with adventitial vacuoles, in a few muscle cells in the heart (not shown), as well as in the subendothelial space of a pulmonary vein (not shown). Uninfected and irradiated mice fed either an atherogenic or a normal diet showed no pathological changes.

These results provide the first evidence that acute MCMV infection induces an inflammatory response in the aortic wall of mice, resembling early AT lesions found in humans.

EXAMPLE 7

Influence of MCMV on Lipid Metabolism

To test how MCMV infection influences the lipid metabolism of mice fed an atherogenic or normal diet, sera were obtained from mice, and total cholesterol (TC) and high density lipoprotein cholesterol (HDL-C) determined. Results showed that TC levels in mice infected but fed normal diet were very similar to those in the naive mice, while TC levels were higher in mice fed the cholesterol diet, either infected or uninfected.

The results also showed that MCMV-infected normocholesterolemic mice had a significantly higher percentage of LDL-C in the serum than naive mice. Similarly, significantly higher LDL-C levels were found in mice fed an atherogenic diet and infected than in mice fed the same diet but uninfected. The results indicate that MCMV infection in mice disturbs lipid metabolism and shifts it to higher levels of LDL-C.

EXAMPLE 8

Effects of *C. pneumoniae* Infection

Figure 3A:
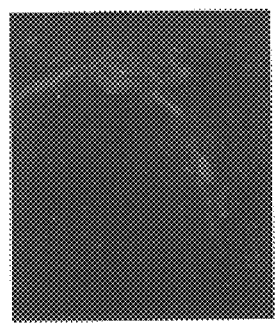
FIG. 3A illustrates *C. pneumoniae* antigens in the aorta of mice infected with *C. pneumoniae*, detected with IF, using a monoclonal antibody specific for the major outer membrane protein (MOMP), dilution 1:5 (DAKO Diagnostic Ltd., Great Britain) and Texas-red-labeled second antibody (Chemicon).
Figure 3B:
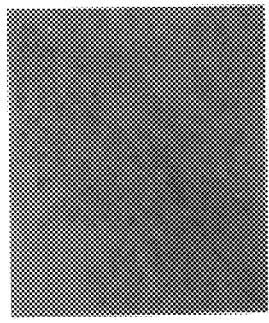
FIG. 3B illustrates an early AT plaque in the aorta of mice infected with *C. pneumoniae*, detected with H&E, magnification ×1250.

BALB/c and C57BL/6 mice were infected intranasally with *C. pneumoniae* ($10^7$ TCID$_{50}$) and sacrificed on days 3, 7, 11, and 27. Hearts were obtained and sectioned for *C. pneumoniae* antigen expression and pathological changes. FIG. 3A shows expression of *C. pneumoniae* antigens in the aortic wall and FIG. 3B shows an inflammatory reaction at the site of *C. pneumoniae* replication.

Figure 4A:
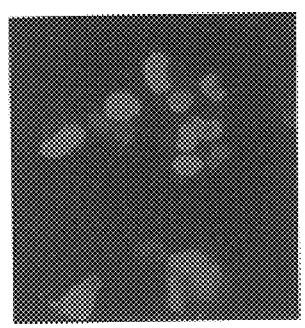
FIG. 4A illustrates the expression of HCMV-IE antigens in human arterial smooth muscle cells, detected with IF, using the E13 monoclonal antibody, dilution 1:80 (Chemicon, USA) and FITC-labeled second antibody.
Figure 4B:
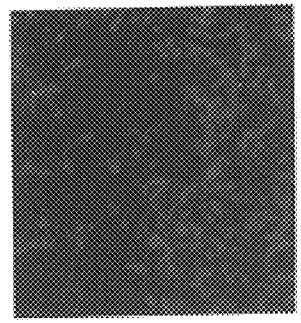
FIG. 4B illustrates the expression of *C. pneumoniae* antigens in human arterial smooth muscle cells, detected with IF, using monoclonal antibody MOMP, and Texas-red-labeled second antibody.

Human arterial smooth muscle cells (HASMC, obtained from Dr. E. Levine, The Wistar Institute) infected with human CMV (HCMV) or *C. pneumoniae* expressed HCMV antigens (FIG. 4A) or *C. pneumoniae* antigens (FIG. 4B), indicating the replication of each pathogen in these cells.

EXAMPLE 9

The Causative Role of Acute and Reactivated CMV Infection in the Initiation and Development of Early and Mature AT Plaques The following experiment is conducted to establish to what extent latent and reactivated MCMV infection, alone or in combination with an atherosclerotic diet, increases the number and severity of AT plaques in mice, and to analyze the role of CMV and contribution of hypercholesterolemia to the development of AT initiated by CMV.

A. Sixteen groups (see Table 1) of C57BL/6 normal female mice (even-number and odd-number groups of 30 and 40 mice, respectively, 8–10 weeks of age, Charles Rivers Laboratory) with no genetic disorders are infected i.p. with MCMV grown previously in salivary glands, at a dose $1 \times 10^4$ pfu/mouse. A group of these mice are immunosuppressed by γ-irradiation (450 rads) at the time of infection and a group of these mice are not irradiated. Each group is then fed an atherogenic or a normal diet throughout the experiment.

Mice in even-number groups are further irradiated (450 rads) 2 times during the observation period of 300 days to reactivate latent CMV infection. The in vivo mouse model for the acute (infectious virus detectable), latent infectious virus no longer detectable), and reactivated (infectious virus detectable again) phases of MCMV infection in the salivary glands, lungs, spleens, and kidneys has already been developed.

Ten mice of odd-number groups (acute infection) are sacrificed on days 25, 50, 225, and 300, while 10 mice of even-number groups (latent or reactivated infection) are sacrificed on days 125, 225, and 300. Hearts are then processed: (i) for the qualitative and quantitative evaluation of AT plaques and for the determination of lipid accumulation by staining sections of aorta with H&E and oil red O; (ii) for the presence of MCMV antigens in sections by immunofluorescence assay using hyperimmune serum from MCMV-infected mice; (iii) for the presence of viral mRNA and DNA during acute, latent, and reactivated stages of infection using RNA and DNA extracted from the upper part of the hearts (not sectioned) for RT-PCR and PCR analysis with appropriate primers for the immediate early or late genes; (iv) for the expression of mRNA and/or proteins of the Hsp family, and growth factors, cytokines, adhesion molecules, e.g., vascular endothelial growth factor, $Le^x$, ICAM-1, VCAM-1, NO, IL-12, IL-8, IL-10, and IFN-γ.

Mouse sera are tested for the percentage of LDL-C by determining TC and HDL-C, as well as for serum ICAM-1 and serum VCAM-1 by ELISA.

Analysis of the aorta obtained from genetically normal mice reveals the extent to which acute MCMV infection initiates the development of early AT plaques; whether a latent MCMV infection with periodic reactivations, a common characteristic of HCMV infections in humans, furthers early plaques into mature, complicated plaques. The influence of a cholesterol diet applied throughout the experiment is evaluated, and immunosuppression applied at the time of infection to prolong initial virus replication, on the number and severity of AT plaques in the aorta.

Finally, the extent to which MCMV immediate early and late gene DNA and mRNA are present in the acute, latent, and reactivated stages of infection in the aortic wall of the mice is observed and the cellular mechanisms involved in the development of AT.

Analysis of mouse sera provides further information about the pathomechanisms of this complex disease, and is predicted to reveal that acute and chronic MCMV infection shifts lipid metabolism to a high percentage of LDL-C in genetically normal mice, as suggested by the preliminary experiments.

B. ApoE-deficient and/or LDL receptor-deficient mice (Jackson Laboratories) are infected or uninfected, and treated as described for normal mice in odd-number groups in Table 1. Each group consists of 10 mice, of which 5 are sacrificed on day 25 and 5 are sacrificed on day 50 after initial infection and treatment. Hearts and sera are obtained and examined as described for genetically normal mice.

The qualitative and quantitative analysis of AT plaques, as well as the kinetics of development, indicate how MCMV infection alters the number and complexity of these plaques in the genetically hypercholesterolemic mice, which show strong similarities to genetic deficiencies in humans. Since the genetically hypercholesterolemic mice develop mature AT plaques after MCMV infection, the ratio of apoptotic cells is determined by terminal-deoxynucleotidyl transferase mediated DNA-end labeling (TUNEL).

Preliminary results show that MCMV replicates in the aortic wall of BALB/c and C57/BL mice

TABLE 1

Treatment protocol for normal mice

| | Immediate treatment | | | Days of virus reactivation by γ-irradiation | |
|---|---|---|---|---|---|
| Groups | I* | D* | G* | 100 | 200 |
| 1 | + | — | — | — | — |
| 2 | + | — | — | + | + |
| 3 | + | — | + | — | — |
| 4 | + | — | + | + | + |
| 5 | + | + | — | — | — |
| 6 | + | + | — | + | + |
| 7 | + | + | + | — | — |
| 8 | + | + | + | + | + |
| 9 | — | — | + | — | — |
| 10 | — | — | + | + | + |
| 11 | — | + | — | — | — |
| 12 | — | + | — | + | + |
| 13 | — | + | + | — | — |
| 14 | — | + | + | + | + |
| 15 | — | — | — | — | — |
| 16 | — | — | — | + | + |

*I - intraperitoneal infection with MCMV; D = cholesterol diet; G = γ-irradiated

EXAMPLE 10

Contribution of Coinfection with MCMV and C. pneumoniae to the Development of AT Lesions Eleven groups of C57/BL6 mice (20/group) (Charles River Laboratory) are infected and treated as outlined in Table 2. Inoculation with the second pathogen is carried out on day 25 after inoculation with the first pathogen to avoid possible interference between the susceptibility of cells to these two pathogens, and to allow sufficient time for the development of an inflammatory response to the first pathogen.

Ten mice are sacrificed 25 days after inoculation with the second pathogen. As controls, mice infected with C. pneumoniae are tested with appropriate antibiotics against C. pneumoniae to establish C. pneumoniae-specificity of the lesions in mice infected with the bacterium, but not treated with antibiotics.

Hearts are processed for qualitative and quantitative evaluation of AT lesions; presence of MCMV and C. pneumoniae antigens in the aortic wall by immunofluorescence assay; presence of cellular Hsp 70 family, vascular endothelial growth factor, $Le^x$, ICAM-1, VCAM-1, NO, IL-12, IL-8, IL-10, and IFN-γ, and presence of apoptotic cells in the lesions by TUNEL.

Sera are processed for determination of TC and LDL-C levels; and serum ICAM-1, serum VCAM-1 levels and Hsp 70 antibodies. Lungs and livers are processed for infectious MCMV and *C. pneumoniae*.

These analyses show whether the injury initiated by MCMV infection progresses to accelerated and/or more complicated lesions as a result of *C. pneumoniae* superinfection, and whether primary *C. pneumoniae* infection initiates aortic wall injury that develops into AT upon secondary MCMV infection. Also, these analyses show whether MCMV or *C. pneumoniae*-induced apoptosis is involved in the development of mature plaques, and whether cellular molecules are induced that are involved in the development of AT.

A decrease of susceptibility of aortic wall (or the whole mouse) to the second pathogen due to induction of some cellular factors (e.g. IFN-α) by the first pathogen is expected to be only transient. Scheduling the second infection at different times after the first infection overcomes this difficulty.

TABLE 2

Treatment protocol for MCMV- and *C. pneumoniae*-coinfected mice

| | Immediate treatment | | Later Treatment | |
|---|---|---|---|---|
| Groups | Infection | γ-irradiation | Infection | γ-irradiation |
| 1 | MCMV | + | *C. pneumoniae* | — |
| 2 | MCMV | + | — | — |
| 3 | — | + | *C. pneumoniae* | — |
| 4 | — | — | *C. pneumoniae* | — |
| 5 | — | + | — | — |
| 6 | *C. pneumoniae* | — | MCMV | + |
| 7 | *C. pneumoniae* | — | — | — |
| 8 | — | — | MCMV | + |
| 9 | — | — | MCMV | — |
| 10 | — | — | — | + |
| 11 | — | — | — | — |

EXAMPLE 11

Coinfection of Human Arterial Endothelial and Smooth Muscle Cells in vitro with HCMV and *C. pneumoniae* Influences Their Replication Both HCMV and *C. pneumoniae* replicate in human arterial endothelial and smooth muscle cells. The interaction between the replication of these two pathogens and the effects of the coinfecting pathogens on the infected endothelial, smooth muscle, or any other cells are addressed as follows.

A. Coinfection Experiments

The following cells cultures: (a) human aortic endothelial cells (obtained from Dr. Jay Nelson, Oregon Health Sciences University, Portland, Oreg.); (b) human iliac arterial endothelial cells; and (c) human iliac arterial smooth muscle cells (both obtained from Dr. Eliott Levine, The Wistar Institute), are treated as follows.

Cell cultures are infected with HCMV and *C. pneumoniae* simultaneously. Other cell cultures are infected consecutively (with HCMV followed by *C. pneumoniae*, with *C. pneumoniae* followed by HCMV. Still another set of cell cultures is infected with only one of these pathogens. Control cultures are uninfected.

Co-infected cultures are tested for replication kinetics of the two pathogens, by quantitating the expression of *C. pneumoniae* and CMV-immediate antigens (IE) in immunofluorescence tests using monoclonal antibodies specific to these antigens, and by quantitating the production of infectious CMV and *C. pneumoniae* in susceptible cell cultures. The quantitative expression of various adhesion molecules are tested by immunochemical staining. Production of various cellular factors, including the Hsp60 family, NO synthetase, and vascular endothelial growth factor are tested by immunological methods. The ratio of apoptotic cells in infected cultures is tested by sodium-iodide staining with subsequent flow-cytometric determination of the percentage of hypodiploid-nuclei.

For assessment of colocalization of apoptotic cells with infected cells, a double-staining process including TUNEL and pathogen-specific immunostaining is performed. Adhesion molecules, as well as Hsp60, are thought to be involved in the development of AT. The presence of apoptotic cells in human AT lesions has been demonstrated and MCMV is known to induce apoptosis of T cells.

These experiments reveal: (a) how these two pathogens influence the replication of each other; (b) how the expression of adhesion molecules and various cellular factors is influenced by these co-infecting pathogens, as compared with that of the single pathogen-infected cultures; and (c) how apoptosis is induced by the two pathogens in cells infected with one pathogen or with two pathways sequentially.

B. Transfection and Infection

Because the human CMV-IE proteins, especially the IE2 protein, are potent transactivators of heterologous promoters, *C. pneumoniae* replication and the production of adhesion molecules and various growth factors in cell lines stably transfected with eukaryotic expression plasmids expressing the IE1 and 2 (pRL43a) or only the IE2 protein of HCMV (pMC18) [both obtained from Dr. Gary Hayward of Johns Hopkins University, Baltimore, Md.)] are analyzed. A stably transfected rhabdomyoma cell line was transfected with these plasmids. The parental cell lines are tested for susceptibility to *C. pneumoniae* infection. Stably transfected Hep2 or McCoy cells, which are highly susceptible for *C. pneumoniae* are also transfected.

Transfected cultures are tested for replication of *C. pneumoniae* as well as for the expression of adhesion molecules and various cellular factors and mechanism(s) as described for the co-infection experiments.

All published documents are incorporated by reference herein. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for retarding the development of cytomegalovirus (CMV)-associated atherosclerotic lesions or CMV-associated restenosis in a mammal comprising:

providing a mammal having been previously exposed to CMV; and administering to said mammal an effective amount of a composition comprising a nucleic acid sequence encoding a CMV immediate early protein, wherein said composition expresses said protein in said mammal and retards the development of CMV-associated atherosclerotic lesions or restenosis.

2. The method according to claim 1, wherein said composition comprises a vector comprising said nucleic acid sequence under the control of a regulatory sequence that directs expression of said CMV immediate early protein sequence.

3. The method according to claim 2, wherein said vector is a virus selected from the group consisting of adenovirus and canarypox virus.

4. The method according to claim 2, wherein said vector is a plasmid.

5. The method according to claim 4, wherein said amount is a dose comprising between 50 and 200 micrograms of plasmid per inoculation.

6. The method according to claim 3, wherein said amount is a low dose comprising between $10^5$ to $10^7$ pfu per inoculation.

7. The method according to claim 1, wherein said mammal is human.

8. The method according to claim 1, wherein said mammal has been previously exposed to CMV and has evidence of arterial injury prior to said administering step.

9. A method for retarding the progression of cytomegalovirus (CMV)-associated atherosclerotic lesions or CMV-associated restenosis in a mammal comprising:

administering to a mammal having existing CMV-associated atherosclerotic lesions an effective amount of a composition comprising a nucleic acid sequence encoding a cytomegalovirus (CMV) immediate early protein, wherein said composition expresses said protein in said mammal and retards the progression of CMV-associated atherosclerotic lesions.

10. The method according to claim 9, wherein said composition comprises a vector comprising said nucleic acid sequence encoding said protein under the control of a regulatory sequence that directs the expression of said CMV immediate early protein sequence.

11. The method according to claim 10, wherein said vector is a virus selected from the group consisting of adenovirus and canarypoxvirus.

12. The method according to claim 10, wherein said vector is a plasmid.

13. The method according to claim 12, wherein said amount is a dose comprising between 50 and 200 micrograms of plasmid per inoculation.

14. The method according to claim 11, wherein said amount is a low dose comprising between $10^5$ to $10^7$ pfu per inoculation.

15. The method according to claim 9, wherein said mammal is human.

16. A method for retarding the development of cytomegalovirus (CMV)-associated atherosclerotic lesions or CMV-associated restenosis in a mammal comprising:

providing a mammal having been previously exposed to CMV; and administering to said mammal an effective amount of a DNA plasmid comprising a nucleic acid sequence encoding a CMV immediate early protein, wherein said plasmid expresses said protein in said mammal and retards the development of CMV-associated atherosclerotic lesions or restenosis.

17. A method for retarding the progression of cytomegalovirus (CMV)-associated atherosclerotic lesions or CMV-associated restenosis in a mammal comprising:

administering to a mammal having existing CMV-associated atherosclerotic lesions an effective amount of a DNA plasmid comprising a nucleic acid sequence encoding a cytomegalovirus (CMV) immediate early protein, wherein said plasmid expresses said protein in said mammal and retards the progression of CMV-associated atherosclerotic lesions.

18. A method for retarding the development of cytomegalovirus (CMV)-associated atherosclerotic lesions or CMV-associated restenosis in a mammal comprising:

providing a mammal having been previously exposed to CMV; and administered to said mammal an effective amount of a viral vector comprising a nucleic acid sequence encoding a CMV immediate early protein, wherein said viral vector is selected from the group consisting of an adenovirus vector and a canarypoxvirus vector, and wherein said viral vector expresses said protein in said mammal and retards the development of CMV-associated atherosclerotic lesions or restenosis.

19. A method for retarding the progression of cytomegalovirus (CMV)-associated atherosclerotic lesions or CMV-associated restenosis in a mammal comprising:

administering to a mammal having existing CMV-associated atheroslerotic lesions an effective amount of a viral vector comprising a nucleic acid sequence encoding a cytomegalovirus (CMV) immediate early protein, wherein said viral vector is selected from the group consisting of an adenovirus vector and a canarypoxvirus vector, and wherein said viral vector expresses said protein in said mammal and retards the progression of CMV-associated atherosclerotic lesions.

* * * * *